(12) United States Patent
Trollsas et al.

(10) Patent No.: US 7,771,739 B2
(45) Date of Patent: *Aug. 10, 2010

(54) IMPLANTABLE MEDICAL DEVICES COMPRISING SEMI-CRYSTALLINE POLY(ESTER-AMIDE)

(75) Inventors: Mikael O. Trollsas, San Jose, CA (US); David C. Gale, San Jose, CA (US); Yunbing Wang, Sunnyvale, CA (US)

(73) Assignee: Abbott Cardiovascular Systems Inc., Santa Clara, CA (US)

(*) Notice: Subject to any disclaimer, the term of this patent is extended or adjusted under 35 U.S.C. 154(b) by 82 days.

This patent is subject to a terminal disclaimer.

(21) Appl. No.: 11/824,008

(22) Filed: Jun. 29, 2007

(65) Prior Publication Data

US 2008/0014238 A1 Jan. 17, 2008

Related U.S. Application Data

(60) Provisional application No. 60/817,922, filed on Jun. 30, 2006.

(51) Int. Cl.
*A61K 31/765* (2006.01)
*A61K 9/00* (2006.01)
*A61F 2/06* (2006.01)
*A61P 13/00* (2006.01)
*A61P 35/00* (2006.01)
*A61P 5/00* (2006.01)
*A61P 9/00* (2006.01)

(52) U.S. Cl. ...................... 424/422; 424/78.37; 623/1.2

(58) Field of Classification Search ........................ None
See application file for complete search history.

(56) References Cited

U.S. PATENT DOCUMENTS

| | | | |
|---|---|---|---|
| 4,304,767 A | 12/1981 | Heller et al. | |
| 4,733,665 A | 3/1988 | Palmaz | |
| 4,800,882 A | 1/1989 | Gianturco | |
| 4,886,062 A | 12/1989 | Wiktor | |
| 5,581,387 A | 12/1996 | Cahill | |
| 5,861,387 A | 1/1999 | Labrie et al. | |
| 6,503,538 B1 | 1/2003 | Chu et al. | |
| 6,703,040 B2 | 3/2004 | Katsarava et al. | |
| 7,056,591 B1 | 6/2006 | Pacetti et al. | |
| 7,166,680 B2 * | 1/2007 | DesNoyer et al. | 525/425 |
| 7,202,325 B2 | 4/2007 | Hossainy et al. | |
| 7,220,816 B2 | 5/2007 | Pacetti et al. | |
| 2002/0015720 A1 | 2/2002 | Katsarava et al. | |
| 2005/0106204 A1 | 5/2005 | Hossainy et al. | |
| 2005/0112171 A1 | 5/2005 | Tang et al. | |
| 2005/0137657 A1 | 6/2005 | Pacetti | |
| 2005/0208091 A1 | 9/2005 | Pacetti | |
| 2005/0245637 A1 | 11/2005 | Tang et al. | |
| 2005/0265960 A1 | 12/2005 | Pacetti et al. | |
| 2005/0271700 A1 | 12/2005 | DesNoyer et al. | |
| 2006/0074191 A1 | 4/2006 | Desnoyer et al. | |
| 2006/0089485 A1 | 4/2006 | DesNoyer et al. | |
| 2006/0093842 A1 | 5/2006 | DesNoyer et al. | |
| 2006/0115513 A1 | 6/2006 | Hossainy | |
| 2006/0142541 A1 | 6/2006 | Hossainy | |
| 2006/0147412 A1 | 7/2006 | Hossainy et al. | |

FOREIGN PATENT DOCUMENTS

| WO | WO 2005/121250 | 12/2005 |
|---|---|---|
| WO | WO 2006/050091 | 5/2006 |
| WO | WO 2006/058122 | 6/2006 |

OTHER PUBLICATIONS

U.S. Appl. No. 10/816,072, filed Mar. 31, 2004, Dugan et al.
Chandrasekar et al., *Coronary Artery Endothelial Protection After Local Delivery of 17β-Estradiol During Balloon Angioplasty in a Porcine Model: A Potential New Pharmacologic Approach to Improve Endothelial Function*, J. of Am. College of Cardiology, vol. 38, No. 5, (2001) pp. 1570-1576.
De Lezo et al., *Intracoronary Ultrasound Assessment of Directional Coronary Atherectomy: Immediate and Follow-Up Findings*, JACC vol. 21, No. 2, (1993) pp. 298-307.
Moreno et al., *Macrophage Infiltration Predicts Restenosis After Coronary Intervention in Patients with Unstable Angina*, Circulation, vol. 94, No. 12, (1996) pp. 3098-3102.
Oikawa et al., Mechanisms of Acute Gain and Late Lumen Loss After Atherectomy in Different Preintervention Arterial Remodeling Patterns, *The Am. J. of Cardiology*, vol. 89, (2002) pp. 505-510.
Scully et al., *Effect of a heparan sulphate with high affinity for antithrombin III upon inactivation of thrombin and coagulaton Factor Xa*, Biochem J. 262, (1989) pp. 651-658.
Virmani et al., *Lessons From Sudden Coronary Death a Comprehensive Morphological Classification Scheme for Atherosclerotic Lesions*, Arterioscler Thromb Vasc Biol. (2000) pp. 1262-1275.
International Search Report for PCT/US2007/015366, mailed Jul. 10, 2008, 8 pgs.

* cited by examiner

*Primary Examiner*—Robert A Wax
*Assistant Examiner*—Danah Al-Awadi
(74) *Attorney, Agent, or Firm*—Squire Sanders & Dempsey, LLP

(57) ABSTRACT

The current invention relates to an implantable medical device made of semi-crystalline poly(ester amide) (PEA) polymer.

18 Claims, No Drawings

IMPLANTABLE MEDICAL DEVICES COMPRISING SEMI-CRYSTALLINE POLY(ESTER-AMIDE)

RELATED APPLICATION

This application claims the benefit of and incorporates by reference U.S. Provisional Patent Application No. 60/817,922 which was filed on Jun. 30, 2006.

FIELD

This invention generally relates to implantable medical devices, in particular stents formed from semi-crystalline poly(ester-amide) (PEA).

BACKGROUND

Blood vessel occlusions are commonly treated by mechanical means using implantable medical devices such as stents. Stents can be used not only as a mechanical intervention but also as a vehicle for providing therapeutic agents.

There are several characteristics that are important for implantable medical devices, such as stents, including high radial strength, good fracture toughness, and fast degradation. Some polymers that may be suitable for use in implantable medical devices have potential shortcomings with respect to some of these characteristics, in particular, fracture toughness and degradation rate. Some crystalline or semi-crystalline polymers that are glassy or have a glass transition temperature (Tg) above body temperature are particularly attractive as stent materials due to their strength and stiffness at physiological conditions. Such glassy polymers can be absorbed through chemical degradation, such as hydrolysis. Physiological conditions refer to conditions that an implant is exposed to within a human body. Physiological conditions include, but are not limited to, human body temperature, approximately 37° C. The toughness of such polymers can be lower than desired, in particular, for use in stent applications. For example, polymers such as poly(L-lactide) (PLLA) are stiff and strong, but tend to be brittle under physiological conditions. These polymers can exhibit a brittle fracture mechanism at physiological conditions in which there is little or no plastic deformation prior to failure. As a result, a stent fabricated from such polymers can have insufficient toughness for the range of use of a stent.

Furthermore, some biodegradable polymers have a degradation rate that is slower than desired for certain stent treatments. As a result, the degradation time of a stent made from such polymers can be longer than desired. For example, a stent made from a semicrystalline polymer such as PLLA can have a degradation time between about two and three years. In some treatment situations, a shorter degradation time is desirable, for example, less than 6 months or a year.

Other potential problems with polymeric stents include creep, stress relaxation, and physical aging, which result from relaxation or rearrangement of polymer chains. Creep refers to the gradual deformation that occurs in a polymeric construct subjected to an applied load. Creep, for example, can result in an expanded stent can retracting radially inward, reducing the effectiveness of a stent in maintaining desired vascular patency.

There is, therefore, an on-going need for implantable medical devices made of polymers that meet all criteria for such implements with regard to radial strength, fracture toughness, biodegradation rate, etc. The current invention provides such implantable medical devices

SUMMARY

Thus, in one aspect the present invention is related to an implantable medical device comprising a semi-crystalline poly(ester amide).

In an aspect of this invention, the poly(ester amide) comprises phenylalanine.

In an aspect of this invention, the poly(ester amide) comprising phenyl alanine is selected from the group consisting of:

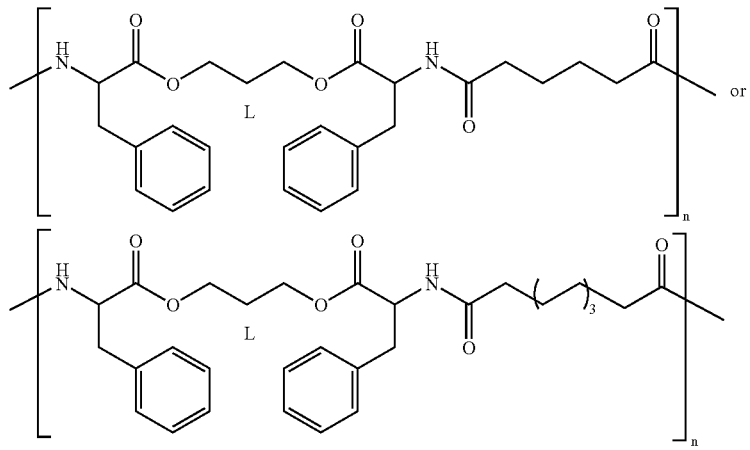

wherein n is a positive integer.

In an aspect of this invention, the semi-crystalline poly(ester amide)polymer has the formula -[A]$_m$-[B]$_n$, wherein A has the structure

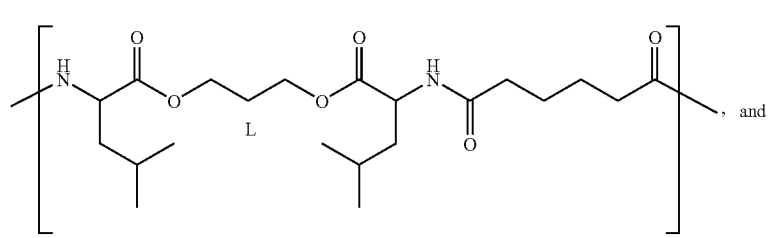

, and

B has the structure

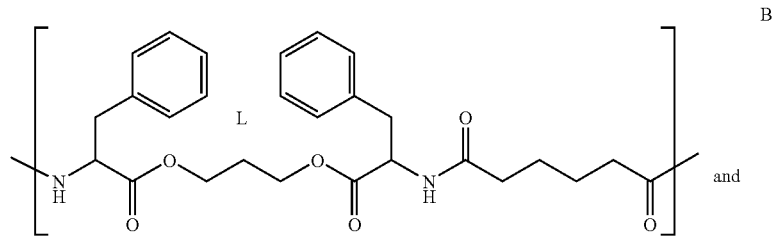

and m, n are independently positive integers of from about 50 to about 1,000,

In an aspect of this invention, the semi-crystalline poly(ester amide) has the structure

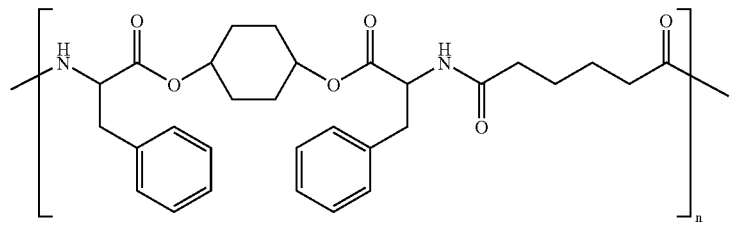

wherein n is a positive integer.

In an aspect of this invention, n is a positive integer of from about 50 to about 1,000.

In an aspect of this invention, the implantable medical device is a stent.

In an aspect of this invention, the stent is a balloon expandable stent.

In an aspect of this invention, the semi-crystalline poly(ester amide) has a formula [A]$_m$-[B]$_n$ wherein [A] and/or [B] comprise a constitutional unit derived from adipate, sebacinate or both and wherein m and n are independent integers of from about 50 to about 1,000.

In an aspect of this invention, the semi-crystalline PEA has a formula of [A]$_m$-[B]$_n$ where [A] and/or [B] comprise a constitutional unit derived from L-leucine, L-valine, isoleucine, DL-norleucine, methionine, l- and dl-phenyl alanine or combinations thereof and wherein m and n are independent integers of from about 50 to about 1,000.

A further aspect of this invention is a method of treating a disease or disorder comprising implanting an implantable medical device of claim 1 in a patient in need thereof.

In an aspect of this invention, in the above method, the disease or disorder is selected from the groups consisting of atherosclerosis, thrombosis, restenosis, hemorrhage, vascular dissection or perforation, vascular aneurysm, vulnerable plaque, chronic total occlusion, claudication, type-II diabetes, anastomotic proliferation for vein and artificial grafts, bile duct obstruction, ureter obstruction and tumor obstruction.

In an aspect of this invention, in the above method, the implantable medical device is a stent and the semi-crystalline poly(ester amide) comprises a constitutional unit derived from phenylalanine.

In an aspect of this invention, in the above method the semi-crystalline poly(ester amide) polymer comprising a constitutional unit derived from phenylalanine is selected from the group consisting of

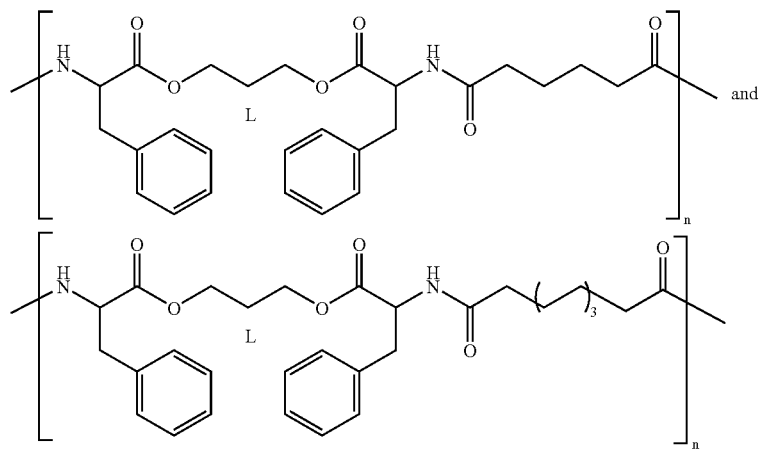

wherein n is a positive integer.

In an aspect of this invention, in the above method, the semi-crystalline poly(ester amide) polymer has a formula $-[A]_m-[B]_n-$, wherein:

m and n are independently positive integers of from about 50 to about 1,000,

A has the structure

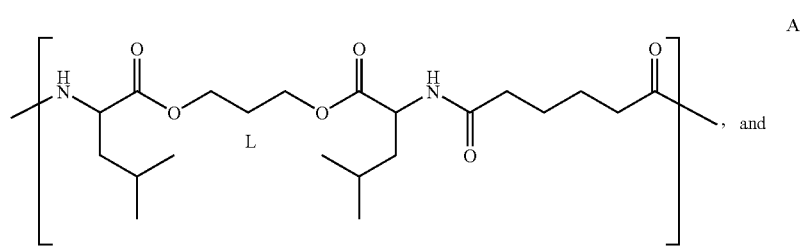

B has the structure

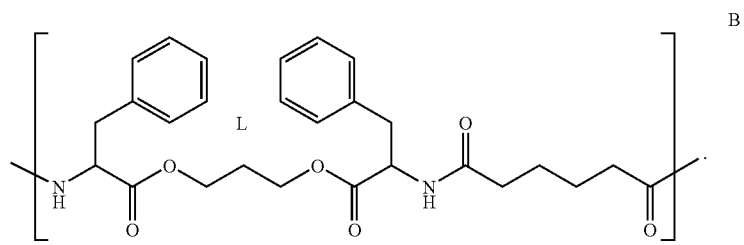

In an aspect of this invention, in the above method, the semi-crystalline poly(ester amide) has the following structure

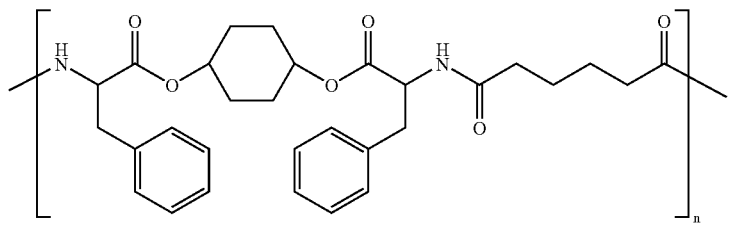

wherein n is a positive integer.

In an aspect of this invention, in the above method, n is an integer from about 50 to about 1,000.

In an aspect of this invention, in the above method the poly(ester amide) comprises a formula of $[A]_m$-$[B]_n$ where [A] and/or [B] comprise a constitutional unit derived from adipate, sebacinate or both and wherein m and n, are independent integers of from about 50 to about 1,000.

In an aspect of this invention, in the above method, the poly(ester amide) has a formula of $[A]_m$-$[B]_n$ where [A] and/or [B] comprises a constitutional unit derived from L-leucine, L-valine, isoleucine, d,l-norleucine, methionine, l- and d,l-phenyl alanine or combinations thereof and wherein m and n, are independent integers of from about 50 to about 1,000.

DETAILED DESCRIPTION

Use of the singular herein includes the plural and visa versa unless expressly stated to be otherwise. That is, "a" and "the" refer to one or more of whatever the word modifies. For example, "a therapeutic agent" includes one such agent, two such agents, etc. Likewise, "the layer" may refer to one, two or more layers and "the polymer" may mean one polymer or a plurality of polymers. By the same token, words such as, without limitation, "layers" and "polymers" would refer to one layer or polymer as well as to a plurality of layers or polymers unless, again, it is expressly stated or obvious from the context that such is not intended.

As used herein, any words of approximation such as without limitation, "about," "essentially," "substantially" and the like mean that the element so modified need not be exactly what is described but can vary from the description by as much as ±15% without exceeding the scope of this invention.

As used herein, an "implantable medical device" refers to any type of appliance that is totally or partly introduced, surgically or medically, into a patient's body or by medical intervention into a natural orifice, and which is intended to remain there after the procedure. The duration of implantation may be essentially permanent, i.e., intended to remain in place for the remaining lifespan of the patient; until the device biodegrades; or until it is physically removed. Examples of implantable medical devices include, without limitation, implantable cardiac pacemakers and defibrillators; leads and electrodes for the preceding; implantable organ stimulators such as nerve, bladder, sphincter and diaphragm stimulators, cochlear implants; prostheses, vascular grafts, self-expandable stents, balloon-expandable stents, stent-grafts, grafts, artificial heart valves and cerebrospinal fluid shunts. An implantable medical device specifically designed and intended solely for the localized delivery of a therapeutic agent is within the scope of this invention.

The present invention relates to implantable medical devices formed from biodegradable semi-crystalline PEAs.

While the implantable medical device can be of any type or for any use where strength, durability and biodegradability are required, a presently preferred such device is a stent. Thus, for the remainder of this discussion only stents will be referred to but it is understood that the disclosures herein apply to all medical devices that might benefit from this invention, that is, all such implantable medical devices are within the scope of this invention.

The semi-crystalline PEAs herein have improved physical properties and, further, are capable of hydrogen bonding, which tends to stabilize the orientation of a polymer chain in a stent. Stents comprising semi-crystalline PEAs would be expected to exhibit biodegradation rates superior to currently used polymers such as poly(L-lactide). Further, as mentioned previously, the ability of PEAs to hydrogen bond is expected to result in improved device toughness. Semi-crystalline PEA stents are also expected to exhibit improved shelf life stability.

A semi-crystalline PEA of this invention may be a homopolymer, a copolymer or a comb polymer. If a copolymer is selected it can be comprised of amorphous domain(s) and a crystalline domain(s). A comb polymer can be comprised of substantially amorphous PEA backbone with crystalline pendent oligomers.

A key constituent of a PEA of this invention is one or more amino acid(s). In general any amino acid may be use; however, at present it is preferred that the amino acids be selected from the group commonly known as the standard amino acids or sometimes the proteinogenic amino acids because they are encoded by the normal genetic code. There currently are 20 standard amino acids: alanine, arginine, asparagine, aspartic acid, cysteine, glutamic acid, glutamine, glycine, histidine, isoleucine, leucine, lysine, methionine, phenyl alanine, proline, serine, threonine, tryptophan, tyrosine and valine. Relatively recently selenoadenine has been found to be incorporated into a number of proteins and is included with the above as a particularly useful amino acid of this invention. In naturally-occurring biological proteins, these amino acids appear as the l-enantiomeric isomers but for the purposes of this invention they may be used as their l- or d-enantiomers, as a racemic (1:1 l:d) mixture or as non-racemic (any mixture of enantiomers other than the 50/50 mix of a racemic mixture).

A presently preferred amino acid component of a PEA of this invention is phenylalanine. Non-limiting examples of phenylalanine PEAs of this invention are the following:

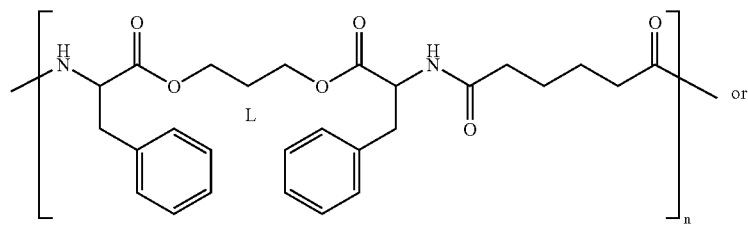

$T_g = 47\text{-}50° \text{C}.$

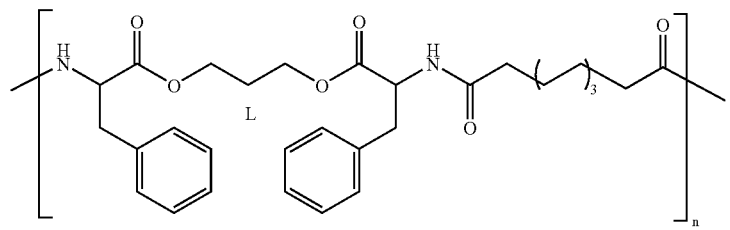

$T_g = 31\text{-}48° \text{C}.$ wherein n is a positive integer.

In some embodiments, the semi-crystalline PEA can be a copolymer comprising non-racemic phenylalanine monomers. The copolymer can be random or block but preferably at present block. The copolymer has the generic formula $-[A]_m-[B]_n-$ where m and n are independent positive integers. A non-limiting example of such a polymer is the following:

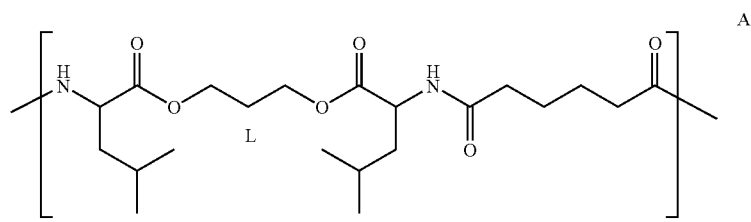

A

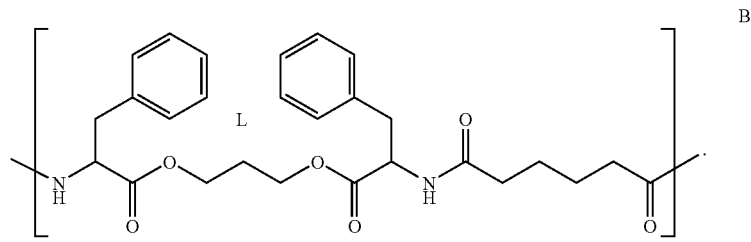

B

As used herein, a poly(ester-amide) refers to a polymer that has in its backbone structure both ester and amide bonds. The poly(ester-amides) of this invention have the generic formula:

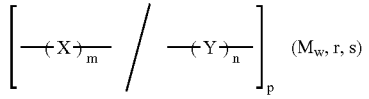

$(M_w, r, s)$ wherein X and Y are the constitutional units of the polymer. In the above formula, m and n are integers that represent the average number of constitutional units X and Y in an uninterrupted string, i.e., the number of X units before a Y unit is encountered, etc. The integers m and n can be any number, including 0, in which case the resulting poly(ester-amide) would be a homopolymer.

As used herein, the term "constitutional unit" refers to the repeating units that make up the polymer. For example, in the following poly(ester-amide) of this invention:

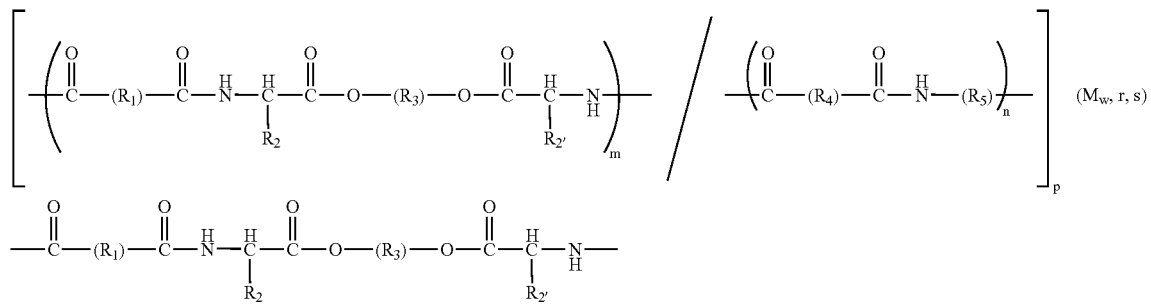

is the X constitutional unit and

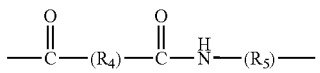

is the Y constitutional unit. The constitution units on the other hand may themselves be comprised of the reaction product of other compounds. For example, without limitation, the X constitutional unit above can result from the reaction of an amino acid,

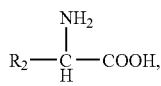

with a diol, HO—($R_3$)—OH, to give a diamino ester,

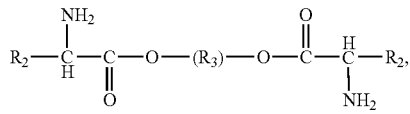

which is then reacted with a diacid,

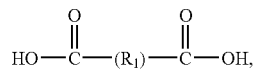

to give the constitutional unit. The amine group, the carboxylic acid group or the hydroxyl group may be "activated," i.e., rendered more chemically reactive, to facilitate the reactions if desired; such activating techniques are well-known in the art and the use of any such techniques is within the scope of this invention. A non-limiting example of the synthesis of an exemplary but not limiting X constitution unit having the above general structure is the reaction of 1,6-hexane diol with l-leucine to give the diamino diester, which is then reacted with sebacic acid to give X. Constitutional unit Y can be obtained by the same reactions as those affording X but using one or more different reactants such that the resulting constitutional units X and Y are chemically different or Y may result from the reaction of a diacid with a tri-functional amino acid wherein two of the functional groups are capable of reacting with the diacid. As example of the foregoing would be the reaction of sebacic acid or an activated derivative thereof, with l-lysine, i.e., 2,6-diaminohexanoic acid.

With regard to the synthesis of the poly(ester-amide)s of this invention, it will be noted that very few reactions or reaction conditions are exemplified herein. This is because the reactions and reaction conditions both for the preparation of constitutional units and for the preparation of the final poly(ester-amide) are standard organic and polymer chemistry well-known to those of ordinary skill in the art and, therefore, those skilled artisan would be able to prepare any of the compounds herein without undue experimentation based on the disclosures herein.

The constitutional units of PEAs of this invention include, in addition to the amino acids described above, polyols, in particular diols, polyamines, in particular diamines and polyacids, in particular diacids and hydroxyacids.

Non-limiting examples of useful polyols are diols having the formula HO—X—OH include those wherein X is selected from the group consisting of straight or branched chain alkylene group having from 2 to 16 carbon atoms in the chain or a cyclic group having from 3 to 16 carbon atoms in the ring(s). Non-limiting examples of alkyene groups include methylene (—$CH_2$—), ethylene (—$CH_2CH_2$—), propylene (—$CH_2CH_2CH_2$—), 2-methylpentylene ($CH_3CH(CH_3)$$CH_2CH_2$—) and the like. Examples of cyclic groups include, without limitation, 1,2-cyclopropylene, 1,4-cyclohexylene, 1,5-decalin (perhydronaphthylene) and the like. Other useful diols include ethylene glycol, diethylene glycol, triethylene glycol, tetraethylene glycol, pentaethylene glycol, 1,3-cyclohexanediol, 1,3-propanediol, 1,4-butanediol, 1,4-cyclohexanediol, cyclohexane-1,4-dimethanol, 1,5-pentanediol, 1,6-hexanediol, 1,7-heptanediol, 1,8-octanediol, 1,9-nonanediol, 1,10-decanediol, 1,11-undecanediol, and 1,12-dodecanediol.

Non-limiting examples of useful polyamines are diamines having the formula $H_2N$—Y—$NH_2$ wherein Y is the same as X. A specific example of useful diamine include 1,4-butanediamine (putrescine), 1,2-ethanediamine, 1,5-pentanediamine (cadavarene) and 1,4 cyclohexanediamine.

Exemplary constitutional units that may be used to synthesize PEAs of this invention include:

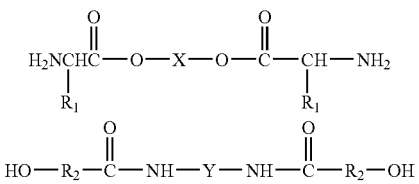

wherein:
X and Y are as described above,
$R_1$ is selected from the group consisting of
  (a) hydrogen;
  (b) methyl (—$CH_3$);
  (c) iso-propyl (-i-$C_3H_7$);
  (d) sec-butyl (-sec-$C_4H_9$);
  (e) iso-butyl (-i-$C_4H_9$); or
  (f) benzyl (—$CH_2C_6H_5$);
$R_2$ is selected from the group consisting of
  (a) methylene (—$CH_2$—);
  (b) ethylene (—$CH_2CH_2$—);
  (c) methylmethylene [—$CH(CH_3)$—];
  (d) straight chained or branched propylene, such as:
    (d1) n-propylene (—$CH_2CH_2CH_2$—);
    (d2) iso-propylene [—$CH_2CH(CH_3)$—]; or
    (d3) ethylmethylene [—$CH(CH_2CH_3)$—];
  (e) straight chained or branched butylene, such as:
    (e1) n-butylene (—$CH_2CH_2CH_2CH_2$—),
    (e2) iso-butylene [—$CH_2CH(CH_3)CH_2$—], or
    (e3) sec-butylene [—$CH(CH_2CH_3)CH_2$—];
  (f) straight chained or branched pentylene, such as:
    (f1) n-pentylene (—$CH_2CH_2CH_2CH_2CH_2$—),
    (f2) iso-pentylene [—$C(CH_3)_2CH_2CH_2$—],
    (f3) neopentylene {—$CH[C(CH_3)_3]$—},
    (f4) 2-methyl-1-butylene [—$C(CH_3)(CH_2CH_3)CH_2$—],
    (f5) sec-iso-pentylene [—$C(CH_3)_2CH(CH_3)$—], or
    (f6) methylpropylmethylene [—$C(CH_3)(CH_2CH_2CH_3)$—]; or
  (g) groups that are present in some amino acids, such as:
    (g1) methyleneamide (present in asparagine) [—$CH_2(CONH_2)$—];
    (g2) ethyleneamide (present in glutamine) [—$CH_2CH_2(CONH_2)$—];
    (g3) methylmercaptomethylmethylene (present in methionine) [—$CH_2(CH_2SCH_3)$—]; or
    (g4) n-propyleneamino group (—$CH_2CH_2CH_2NH$—) which can be derived from 2-pyrrolidine group present (present in proline);
  (h) aromatics;
  (i) estradiol; and,
  bis-MPA (2,2,-dimethylolpropionic acid) derivatives and similar compounds with protected free acids.

Specific examples of hydroxyacids that are useful to prepare the PEAs of this invention include, without limitation, glycolic acid, lactic acid, β-hydroxypropionic acid, β-hydroxybutyric acid, α-hydroxyvaleric acid, β-hydroxyvaleric acid, ε-hydroxycaproic acid, α-hydroxycaproic acid, β-hydroxycaproic acid and δ-hydroxycaproic acid, During the synthesis of some of the constitution units of this invention one of more groups may have to be "blocked" or "protected"—the terms are synonymous in the art—to avoid undesired reactions taking place. Techniques for blocking and unblocking functional groups are extremely well-known in the synthetic chemical and polymer arts and require no further discussion. For example, a vast group of blocking groups and method of their use may be found in the ubiquitous compendium Protective Groups in Organic Synthesis, 4$^{th}$ Edition, Peter G. M. Wuts, Theodora W. Greene ed., Wiley, 2006).

Useful diacids for synthesizing constitutional units of this invention may have the formula

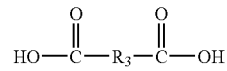

wherein $R_3$ is selected from the same moieties set forth above with regard to "X" but in addition may also be selected from the group consisting of a single bond or an aromatic group such as, without limitation phenyl or naphthyl. The $R_3$ group may be unsubstituted or substituted with one or more hydroxy groups which may be blocked during the synthesis of the constitutional unit of the PEA itself and subsequently deblocked.

Useful diacids for preparing constitutional units of this invention include, without limitation, oxalic acid, malonic acid, glutaric acid, pimelic acid, suberic acid, azelaic acid, succinic acid, adipic acid, sebacic acid, terephthalic acid and cyclohexane-1,4-dicarboxylic acid.

The subscripts m and n, which represent the number of repeats of the moiety within the brackets, are independent integers from about 50 to about 1,000. "P" is likewise an independent integer of from about 1 (a diblock polymer) to about 3000.

A PEA stent of this invention may be, without limitation, a balloon expandable stent, a self-expandable stent or a braided stent. The stent may be used for a variety of interventional or endovascular medical procedures including, but not limited to, angioplasty, treatment of obstructions caused by tumors in the bile ducts, esophagus, trachea/bronchi and other biological passageways. The stent may be intended for implantation in an artery or a vein as treatment requires. Further, a PEA stent of this invention may be use as a drug-eluting stent. That is, the PEA stent itself may have one of more therapeutic agents impregnated into its structure or the PEA stent may be coated with other polymeric materials containing the therapeutic agent(s). Any therapeutic agent capable of treating the disease or disorder at the implantation site of the stent may be used but of particular use are therapeutic agents that mitigate abnormal or inappropriate migration and proliferation of smooth muscle cells, restenosis, therosclerosis, thrombosis, restenosis, hemorrhage, vascular dissection or perforation, vascular aneurysm, vulnerable plaque, chronic total occlusion, claudication, type-II diabetes, anastomotic proliferation for vein and artificial grafts, bile duct obstruction, ureter obstruction, tumor obstruction and the like.

EXAMPLES

Example 1

Synthesis of Di-ρ-toluenesulfonic Acid Salts of bis(L-Phenylalanine) α,ω-propane Diester Phenylalanine (2 mol) and propanediol (1 mol) are condensed in refluxing toluene at 134° C. in the presence of ρ-toluenesulfonic acid monohydrate (2 mol). The product is a

Example 2

Synthesis of di-ρ-nitrophenyl adipate

Di-ρ-nitrophenyl adipate is prepared by reacting adipoyl chloride (1 mol) with ρ-nitrophenol (2.01 mol) in ethyl acetate in the presence of triethylamine (2.01 mol) at room temperature. The resulting di-ρ-nitrophenyl ester is purified by repeated recrystallization from acetone.

Example 3

Synthesis of PEA having Constitutional Units from Examples 1 and 2

The monomer of Example 1 (1 mol) and the monomer of example 2 (1 mol) are stirred at 60° C. for 25 h in DMF (1:1 monomer:solvent ratio). The product is precipitated by pouring into a 5-10-fold excess (by volume) of distilled water. The liquid is decanted and the remaining polymer is washed three to four times with distilled water and collected by filtration using a glass filter. The polymer is then dissolved into chloroform and the residue water is removed using magnesium sulfate. The magnesium sulfate is removed by filtration and the polymer re-precipiated by pouring the solution into diethyl ether. The product is isolated by filtration and dried to constant weight in a vacuum oven at 60° C.

Example 4

Synthesis Di-ρ-toluenesulfonic Acid Salts of bis(L-Phenylalanine) α,ω-propane Diester Phenylalanine (2 mol) and propanediol (1 mol) are condensed in refluxing toluene in the presence of ρ-toluenesulfonic acid monohydrate (2 mol). The product is a white crystalline substance which is purified by repeated recrystallization from ethanol.

Example 5

Synthesis of di-ρ-nitrophenyl sebacate

Di-ρ-nitrophenyl sebacate is prepared by the reaction of sebacic acid chloride (1 mol) with ρ-nitrophenol (2.01 mol) in ethyl acetate in the presence of triethylamine (2.01 mol) at room temperature. The resulting di-ρ-nitrophenyl ester is purified by repeated recrystallization from acetone.

Example 6

Synthesis of PEA 2 by Solution Polycondensation of the Monomer of Examples 4 and 5

The monomer of Example 4 (1 mol) and the monomer of Example 5 (1 mol) are dissolved in DMF (1:1 monomers:solvent) and stirred at 60° C. for 25 h. The product is precipitated into a 5-10-fold excess (by volume) of distilled water. The liquid is decanted and the residual polymer is washed three to four times with distilled water. The polymer is then isolated by filtration through a glass filter and then dissolved in chloroform after which magnesium sulfate is added to remove residual water. The magnesium sulfate is filtered off and the product is precipitated by pouring the solution into diethyl ether. The precipitated product is isolated by filtration and dried in a vacuum oven at 60° C. to constant weight.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed:

1. An implantable medical device comprising a semi-crystalline poly(ester amide), wherein the poly(ester amide) comprises phenyl alanine, wherein the poly(ester amide) comprising phenyl alanine is selected from the group consisting of:

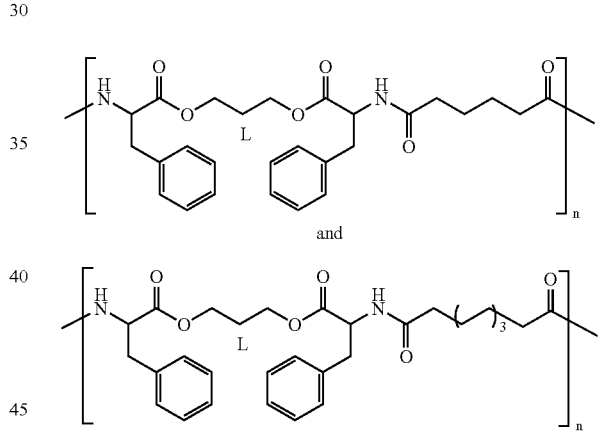

and wherein n is a positive integer.

2. An implantable medical device comprising a semi-crystalline poly(ester amide), wherein the semi-crystalline poly(ester amide)polymer has the formula $-[A]_m-[B]_n$, wherein A has the structure

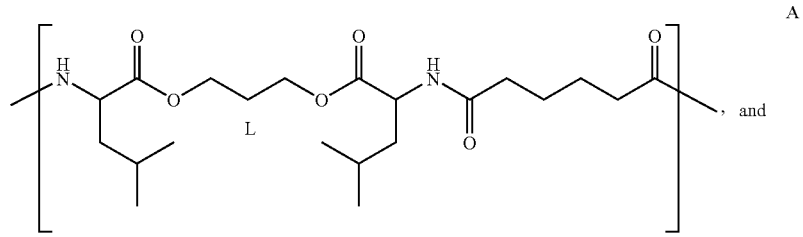

, and has the structure

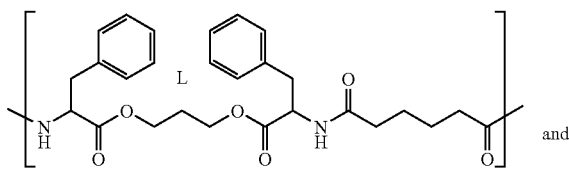

m, n are independently positive integers of from about 50 to about 1,000.

3. An implantable medical device comprising a semi-crystalline poly(ester amide), wherein the semi-crystalline poly(ester amide) has the structure

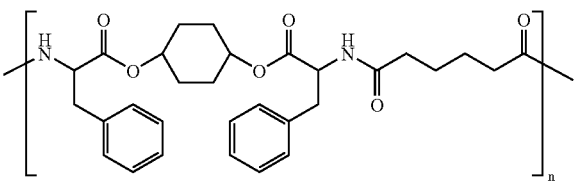

wherein n is a positive integer.

4. The implantable medical device of claim 3, wherein n is a positive integer of from about 50 to about 1,000.

5. The implantable medical device of claim 1, wherein the device is a stent.

6. The biodegradable stent of claim 5, wherein the stent is a balloon expandable stent.

7. An implantable medical device comprising a semi-crystalline poly(ester amide), wherein the semi-crystalline PEA has a formula $[A]_m$-$[B]_n$, wherein [A] and/or [B] comprise a constitutional unit derived from adipate, sebacinate or both and wherein m and n are independent integers of from about 50 to about 1,000.

8. An implantable medical device comprising a semi-crystalline poly(ester amide), wherein the semi-crystalline PEA has a formula of $[A]_m$-$[B]_n$ where [A] and/or [B] comprise a constitutional unit derived from L-leucine, L-valine, isoleucine, DL-norleucine, methionine, l- and dl-phenyl alanine or combinations thereof and wherein m and n are independent integers of from about 50 to about 1,000.

9. A method of treating a disease or disorder comprising implanting an implantable medical device of claim 1 in a patient in need thereof.

10. The method of claim 9, wherein the disease or disorder is selected from the groups consisting of atherosclerosis, thrombosis, restenosis, hemorrhage, vascular dissection or perforation, vascular aneurysm, vulnerable plaque, chronic total occlusion, claudication, type-II diabetes, anastomotic proliferation for vein and artificial grafts, bile duct obstruction, ureter obstruction and tumor obstruction.

11. A method of treating a disease or disorder comprising implanting an implantable medical device of claim 2 in a patient in need thereof.

12. A method of treating a disease or disorder comprising implanting an implantable medical device of claim 3 in a patient in need thereof.

13. A method of treating a disease or disorder comprising implanting an implantable medical device of claim 7 in a patient in need thereof.

14. A method of treating a disease or disorder comprising implanting an implantable medical device of claim 8 in a patient in need thereof.

15. The method of claim 11, wherein the disease or disorder is selected from the group consisting of atherosclerosis, thrombosis, restenosis, hemorrhage, vascular dissection or perforation, vascular aneurysm, vulnerable plaque, chronic total occlusion, claudication, type-II diabetes, anastomotic proliferation for vein and artificial grafts, bile duct obstruction, ureter obstruction and tumor obstruction.

16. The method of claim 12, wherein the disease or disorder is selected from the group consisting of atherosclerosis, thrombosis, restenosis, hemorrhage, vascular dissection or perforation, vascular aneurysm, vulnerable plaque, chronic total occlusion, claudication, type-II diabetes, anastomotic proliferation for vein and artificial grafts, bile duct obstruction, ureter obstruction and tumor obstruction.

17. The method of claim 13, wherein the disease or disorder is selected from the group consisting of atherosclerosis, thrombosis, restenosis, hemorrhage, vascular dissection or perforation, vascular aneurysm, vulnerable plaque, chronic total occlusion, claudication, type-II diabetes, anastomotic proliferation for vein and artificial grafts, bile duct obstruction, ureter obstruction and tumor obstruction.

18. The method of claim 14, wherein the disease or disorder is selected from the group consisting of atherosclerosis, thrombosis, restenosis, hemorrhage, vascular dissection or perforation, vascular aneurysm, vulnerable plaque, chronic total occlusion, claudication, type-II diabetes, anastomotic proliferation for vein and artificial grafts, bile duct obstruction, ureter obstruction and tumor obstruction.

* * * * *